United States Patent [19]
Akiyama et al.

[11] Patent Number: 5,995,282
[45] Date of Patent: Nov. 30, 1999

[54] OPERATION MICROSCOPE

[75] Inventors: Hiroshi Akiyama; Yuichi Sugino, both of Tokyo, Japan

[73] Assignee: Kabushiki Kaisha, Topcon, Tokyo, Japan

[21] Appl. No.: 08/812,213

[22] Filed: Mar. 6, 1997

[30] Foreign Application Priority Data

Mar. 6, 1996 [JP] Japan .................................. 8-049330

[51] Int. Cl.⁶ .................................................. G02B 21/00
[52] U.S. Cl. .......................... 359/384; 359/368; 359/382
[58] Field of Search .................... 359/363, 368, 359/372–384, 689; 351/205–208, 211–219, 221; 250/201.2–201.4

[56] References Cited

U.S. PATENT DOCUMENTS

| | | | |
|---|---|---|---|
| 3,566,872 | 3/1971 | Draeger | 359/384 |
| 3,887,267 | 6/1975 | Heller | 359/384 |
| 4,912,388 | 3/1990 | Tanaka et al. | 359/382 |
| 5,748,366 | 5/1998 | Yasunaga et al. | 359/368 |
| 5,835,266 | 11/1998 | Kitajima | 359/384 |

*Primary Examiner*—Thong Nguyen
*Attorney, Agent, or Firm*—Oppedahl & Larson LLP

[57] ABSTRACT

In an operation microscope, when an observation velocity of an observation field of a main microscope body is set to a desired velocity and then an observation magnification of the observation field of the main microscope body is changed and the focal point thereof is moved, each encoder detects changing of the observation magnification and moving of the focal point and then outputs a detection result to an arithmetic-logic unit. The arithmetic-logic unit calculates the drive condition that a moving velocity of the observation field of the main microscope body after the observation magnification is changed and the focal point is moved is a desired velocity, based on the detection result of each encoder. By using a Y-axis actuator, an X-axis actuator, a vertical direction moving unit and a horizontal direction moving unit, the main microscope body is moved under the control of a CPU in accordance with the drive condition obtained by the arithmetic-logic unit. Thus, the moving velocity of the observation field is automatically kept constant.

10 Claims, 12 Drawing Sheets

PRIOR ART

OPERATION MICROSCOPE

BACKGROUND OF THE INVENTION

1. Field of the Invention

The present invention relates to an operation microscope having a moveable main body unit of the microscope to permit movement of the observation (viewing) field or to change the observation direction.

2. Description of Related Art

In general, operation microscopes are used to observe the affected part in an enlarged manner during medical operations. Also, operation microscopes may function as eyes of operators during operations, and thus are desirably allow the observation fields or observation directions of the operation microscopes to be moved or changed like human eyes. In particular, moving of observation fields and changing of observation directions of these operation microscopes are frequently performed in brain neurosurgical operations.

In general-purpose microscopes used in the brain neurosurgical operations, gravity moments are canceled with each other, and positioning of the observation fields and the observation directions are manually performed. In other words, operators must take their hands off from the affected part every time the observation fields are moved and the observation directions are changed. As a result, the operation time would be prolonged, resulting in overload for not only the operators, but also the patients. To relieve this problem, a mechanism for automatically moving the observation fields and for automatically changing the observation direction is used.

In this case, the mechanism for automatically moving the observation field corresponds to a mechanism for moving an observation field in a fine mode. By this mechanism, moving of the observation field can be performed by using a foot switch without removing a hand of an operator from the affected part. Also, in this observation field moving mechanism, actuators are provided with respect to two mutually perpendicular rotation axes. A main microscope body can be swung by the actuators around the rotation axes. Thus, the focal point of the main microscope body is moved on a spherical surface where the cross point of the rotation axes is at the center of rotation. As a consequence, the observation field can be moved.

In a similar manner, the observation direction can be changed without removing the hand of the operator from the affected part. In this observation direction changing mechanism, the observation direction is changed by swinging the main microscope body, with the focal point of the main microscope body at the center of rotation.

While the medical operation is carried out by using the operation microscope, the focusing is frequently achieved by moving of the main microscope body. For example, as shown in FIG. 14, focusing is carried out by moving the main microscope body 70 along the direction of the observation axis OZ. In this case, the distances between the focal point P of the main microscope body 70 and the moving rotation axes OX and OY are different before and after the main microscope body 70 is moved. As a consequence, even if the rotational velocity (angular velocity) of the main microscope body 70 is constant, the velocity of the focal point P is changed, so that the apparent velocity of the observation field is changed.

Also, when the observation magnification of the observation field is changed from low magnification to high magnification, the observation field appears to be closer to the operator. Thus, the apparent velocity of the observation field is different at different magnifications even if the actual velocity of the focal point P is constant.

Moreover, when the main microscope body unit 70 is rotated about rotation axis OY, perpendicular to the observation axis OZ, so as to move the focal point P, the distance between the focal point P and the moving rotation axis OX perpendicular to the rotation axis OY is changed. As a consequence, after the focal point P is moved by rotation about rotation axis OY perpendicular to the observation axis OZ, if the main microscope body 70 is thereafter rotated, the apparent velocity of the observation field in the case wherein the body 70 is rotated about rotation axis OY is different from that of the observation field in the case wherein the body 70 is rotated about rotation axis OX.

As to the changing velocity of the observation direction, a similar phenomenon to that for the apparent velocity of the observation field will occur.

As described above, the conventional operation microscope has the following problems. When the observation conditions such as the focal position, the focal distance, the observation magnification and the like are changed and the observation states such as the inclination of the main microscope body are changed, either the apparent velocity of the movement of the observation field or the apparent velocity of the change in observation direction depends on before and after these conditions and states are changed. Thus, to maintain a consistent display, the operator must readjust the actual velocity of the main microscope body every time the observation condition or state is changed. This may interfere with a medical operation which needs great urgency.

SUMMARY OF THE INVENTION

The present invention has been made to solve the above problems, and it is an object of the present invention to provide an operation microscope capable of automatically maintaining a constant apparent velocity for changes of the observation direction, and a constant apparent velocity for movement of the observation field, even if either the observation condition or the observation state is varied, and also capable of improving the operability.

To solve the above problems, according to the present invention, there is provided an operation microscope in which an observation field is movable, comprising: a main microscope body supported by a support member and rotatable about a plurality of rotation axes; means for rotating the main microscope body about the rotation axes; means for setting a desired value for the apparent velocity of the movement of the observation field of the main microscope body; means for monitoring the observation condition and observation state of the main microscope body; calculating means for calculating a drive condition that maintains the apparent velocity of the observation field at the desired value when the microscope main body is changed from a first observation condition and observation state to a second observation condition and observation state; and means for controlling the means for rotating the main microscope body in accordance with the drive condition calculated by the calculating means.

With the above structure, in the operation microscope according to the present invention, the changes in the observation condition and the observation state of the main microscope body are obtained, for example by encoders which monitor the position of the main microscope body a drive condition which will produce the desired apparent velocity for movement of the observation field of the main microscope body is calculated by the calculating means based upon the observation condition and the observation state, and the rotating means is controlled in accordance with the calculated drive condition to move the main microscope body.

Further, to solve the above problems, according to the present invention, there is provided an operation microscope in which an observation direction is changeable, comprising: a main microscope body supported by a support member and rotatable about a plurality of rotation axes; means for rotating the main microscope body about the rotation axes; means for setting a desired apparent velocity for changes in the observation direction of the main microscope body; means for monitoring the observation condition and the observation state of the main microscope body; means for calculating a drive condition that maintains the apparent velocity of the change in observation direction of the main microscope body at the desired velocity when the observation condition and the observation state of the main microscope body are changed; and means for controlling the rotating means in accordance with the drive condition calculated by the calculating means.

With the above structure, in the operation microscope according to the present invention, the changes in the observation condition and the observation state of the main microscope body are obtained, a drive condition which will produce the desired apparent velocity for changing the observation direction of the main microscope body is calculated by the calculating means based upon the observation condition and the observation state, and the rotating means is controlled in accordance with the calculated drive condition to move the main microscope body.

DETAILED DESCRIPTION OF THE PREFERRED EMBODIMENTS

Referring now to drawings, an operation microscope according to an embodiment of the present invention will be described in detail.

Figure 1:
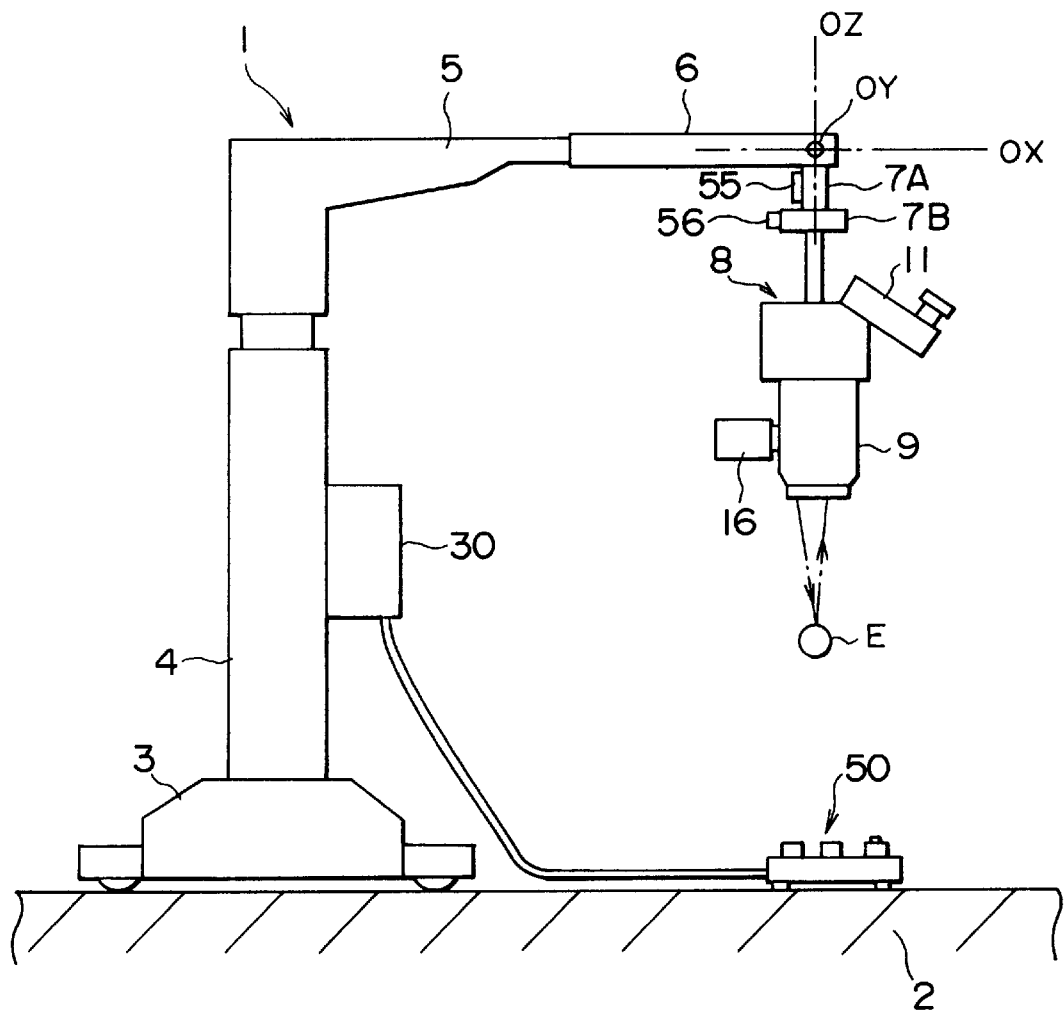
FIG. 1 shows the structure of an operation microscope according to an embodiment of the present invention.

FIG. 1 shows the structure of an operation microscope according to an embodiment of the present invention.

As shown in FIG. 1, an operation microscope 1 is constructed by a supporting member 3 movable on a floor surface 2 in, for example, an operating room, a pillar 4 provided uprightly from the supporting member 3, a first arm 5 supported by the pillar 4, a second arm 6 having one end provided to the first arm 5, a vertical direction moving unit 7A provided in the other end of the second arm 6, a horizontal direction moving unit 7B provided under the vertical direction moving unit 7A, and a main microscope body 8 provided under the horizontal direction moving unit 7B. Further, the operation microscope 1 has a foot switch 50 for arbitrarily setting a moving velocity of the main microscope body 8 while carrying out various sorts of operation of the main microscope body 8.

Figure 2:
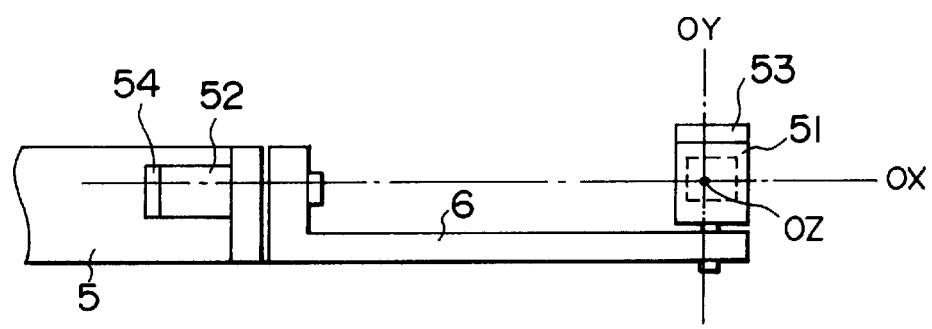
FIG. 2 shows a part of the structure of the operation microscope according to the embodiment of the present invention.

As shown in FIG. 2 that is a view where the second arm 6 shown in FIG. 1 is observed from the above, one end of the second arm 6 is connected via an X-axis actuator 52 to the first arm 5, and the other end of the second arm 6 is connected via a Y-axis actuator 51 to the vertical direction moving unit 7A.

The X-axis actuator 52 causes the second arm 6 to be rotatively driven around the moving rotation axis OX. The main microscope body 8 and the like provided in the second arm 6 are swung around the rotation axis OX by rotatively driving the second arm 6 by the X-axis actuator 52. An X-axis encoder 54 for detecting a rotation angle and an angular velocity of the X-axis actuator 52 is provided on the X-axis actuator 52.

The Y-axis actuator 51 causes the second arm 6 to be rotatively driven around the rotation axis OY. The main microscope body 8 and the like provided in the second arm 6 are swung around the rotation axis OY by rotatively driving the second arm 6 by the Y-axis actuator 51. A Y-axis encoder 53 for detecting a rotation angle and an angular velocity of the Y-axis actuator 51 is provided on the Y-axis actuator 51.

The vertical direction moving unit 7A upwardly/downwardly (vertically) moves the main microscope body 8 along the direction of the observation axis OZ. A vertical direction encoder 55 for detecting the amount of movement of the vertical direction moving unit 7A is provided on the vertical direction moving unit 7A.

The horizontal direction moving unit 7B horizontally moves the main microscope body 8 in a parallel manner along the directions of the rotation axes OY and OX. Since the main microscope body 8 is moved in a parallel manner along the rotation axes OY and OX by the horizontal direction moving unit 7B, the focal position of the main microscope body 8 can be changed. A horizontal direction encoder 56 for detecting the amount of movement of the main microscope body 8 moved by the horizontal direction moving unit 7B is provided on the horizontal direction moving unit 7B.

When the Y-axis actuator 51, the X-axis actuator 52, the vertical direction moving unit 7A or the horizontal direction moving unit 7B is independently driven, the observation (viewing) field of the microscope is changed. When the Y-axis actuator 51 and the X-axis actuator 52 are driven at the same time, the focal point of the main microscope body 8 is moved on a spherical surface where a cross point between the rotation axes OX and OY is located at a center thereof, so that the observation field is changed.

Similarly, when the Y-axis actuator 51 or the X-axis actuator 52, the vertical direction moving unit 7A and the horizontal direction moving unit 7B are driven, the observation direction of the microscope is changed. Changing the observation direction is different from changing the observation field. This means that only the observation direction is changed without changing the observation position, namely a focal position of the main microscope body 8.

Figure 3:
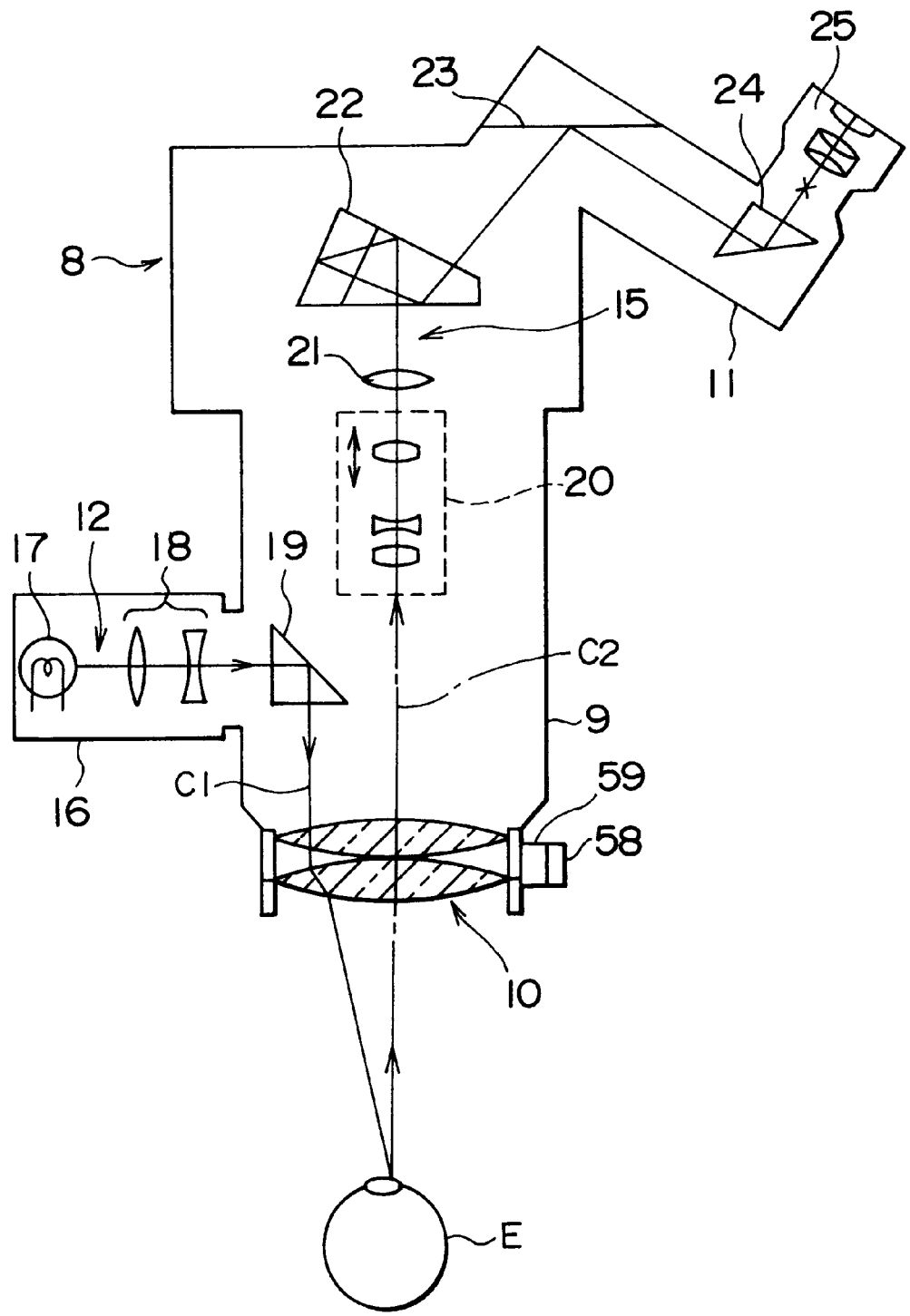
FIG. 3 shows the structure of a main microscope body of the operation microscope according to the embodiment of the present invention.

The main microscope body 8 is constructed by a lens-barrel 9 formed in a cylindrical shape, an eyepiece lens barrel 11 provided in an upper portion of the lens barrel 9 and a lamp house 16 provided on a side portion of the lens barrel 9. As shown in FIG. 3, an objective lens 10 (provided in a lower portion of the lens barrel 9) and an observation optical system 15 are assembled in the lens barrel 9, and an illumination optical system 12 is assembled in the lamp house 16.

The objective lens 10 is an objective lens whose focal distance is variable and constructed by, for example, two lenses. For the objective lens 10, a focal distance changing unit 59 which adjusts the interval between two lenses of the objective lens 10 and is made of various sorts of cams and gears is provided. A focal distance is changed by the focal distance changing unit 59. A changing quantity of the focal distance by the objective lens 10 is detected by an objective lens encoder 58.

The illumination optical system 12 is constructed by a light source 17 such as a halogen lamp provided in the lamp house 16, a collective lens 18 for collecting light emitted from the light source 17 and a prism 19 arranged in the lens barrel 9 for reflecting the light from the collective lens 18 to the side of the objective lens 10. The respective optical elements employed in the illumination optical system 12 and the objective lens 10 form an illumination optical path C1 defined from the light source 17 to an eye E to be examined.

The observation optical system 15 has a variable power optical system 20 which performs afocal variable power operation (afocal magnification changing operation) and is arranged above the objective lens 10, an image lens 21 arranged above the variable power optical system 20, an erecting prism 22 arranged further above the image lens 21, a reflecting mirror 23 arranged in the eyepiece lens barrel 11, a total reflecting prism 24 and an eyepiece lens 25. Also, the observation optical system 15 forms an observation optical path C2 by the respective optical elements. The observation magnification is changed by the variable power operation (magnification changing operation) by the variable power optical system 20.

Figure 4:
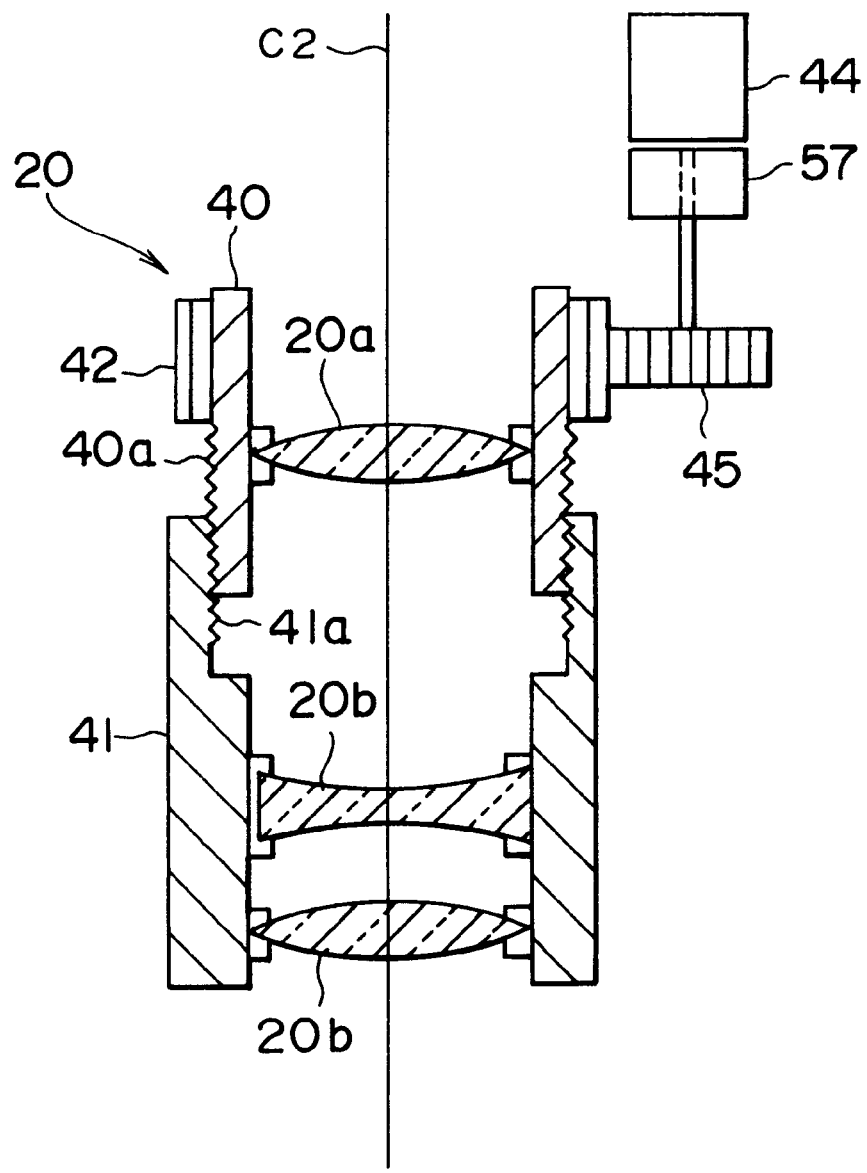
FIG. 4 shows the structure of a variable power optical system of the operation microscope according to the embodiment of the present invention.

As shown in FIG. 4, the variable power optical system 20 has several sorts of lenses 20a and 20b. The respective lenses are fixed inside cylinder portions 40 and 41 by using fixing members. In this case, the cylinder portions 41 partially has a step portion, and then a portion of the cylinder portion 40 is loosely fitted to an inner peripheral portion 41a of the step portion.

Screws are formed in the inner peripheral portion 41a of the step portion of the cylinder portion 41 and the outer peripheral portion 40a of the cylinder portion 40, respectively. These screws are screwed to each other. Further, a gear 42 is formed on the outer peripheral portion 40a of the cylinder portion 40. The gear 42 is meshed with a gear 45 provided in a power shaft of a motor 44. When the gear 45 is rotatively driven by the motor 44, the gear 42 is meshed with the gear 45 and rotated, so that the cylinder portion 40 is relatively slid along the optical axis direction with respect to the cylinder portion 41. As a result, the lens 20a provided in the cylinder portion 40 is relatively slid along the optical axis direction with respect to the lens 20b, and variable power operation is performed by the variable power optical system 20. A moving quantity of the lens 20a along the optical axis direction in the variable power optical system 20 is detected by a variable power encoder 57 arranged in a coaxial manner to the motor 44. The variable power encoder 57 converts the moving quantity of the lens 20a into a pulse signal and then outputs the pulse signal to a CPU 61 (as described below).

Figure 5:
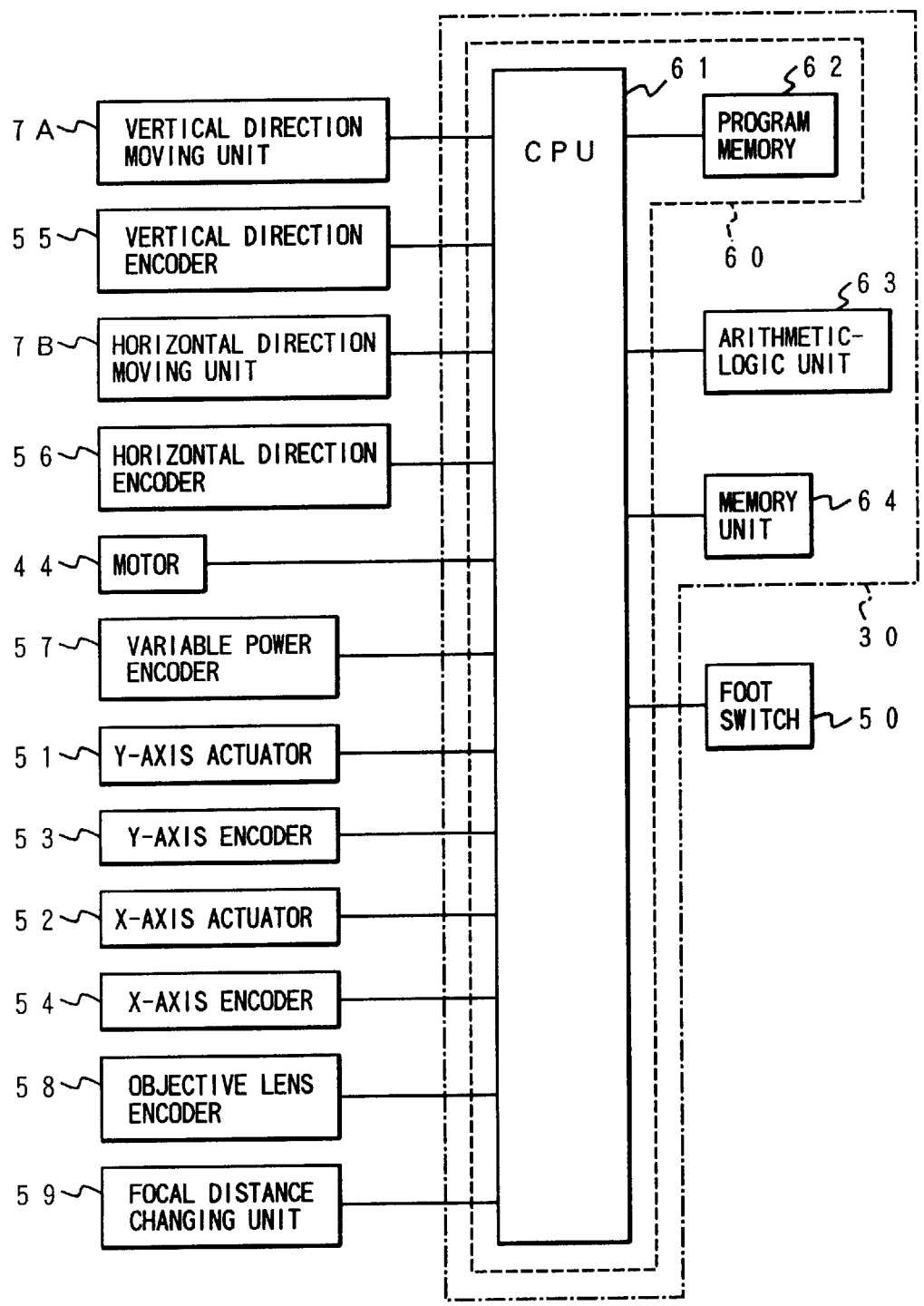
FIG. 5 is a block diagram showing the structure of a control system of the operation microscope according to the embodiment of the present invention.

Referring to FIG. 5, the structure of a control system of the operation microscope 1 will be described.

As shown in FIG. 5, a control system 30 of the operation microscope 1 is constructed by a control unit 60, an arithmetic-logic unit 63 and a memory unit 64. The control unit 60 is constructed by a program memory 62 for storing various sorts of operation programs and the central processing unit (CPU) 61 for controlling operations of the operation microscope 1 based on the operation programs stored in the program memory 62. The CPU 61 of the control unit 60 is connected to the vertical direction moving unit 7A, the horizontal direction moving unit 7B, the motor 44, the Y-axis actuator 51, the X-axis actuator 52, the Y-axis encoder 53, the X-axis encoder 54, the vertical direction encoder 55, the horizontal direction encoder 56, the variable power encoder 57, the objective lens encoder 58, the focal distance changing unit 59, the foot switch 50, the arithmetic-logic unit 63 and the a memory unit 64 for storing various sorts of data. The CPU 61 controls these elements.

The arithmetic-logic unit 63 calculates drive conditions to cause the apparent velocity of movement of the observation field and the observation direction in the main microscope body 8 to be a desired velocity as the observation conditions of the main microscope body 8 and the observation states thereof are changed.

The CPU 61 controls the Y-axis actuator 51, the X-axis actuator 52, the vertical direction moving unit 7A and the horizontal direction moving unit 7B in accordance with the drive conditions calculated by the arithmetic-logic unit 63, so as to move the main microscope body 8.

Next, operations of the operation microscope 1 will now be explained with reference to FIGS. 6 to 9. First, a description is made of operations when the observation magnification is changed by using the variable power optical system 20 during microscopic observation.

Figure 6:
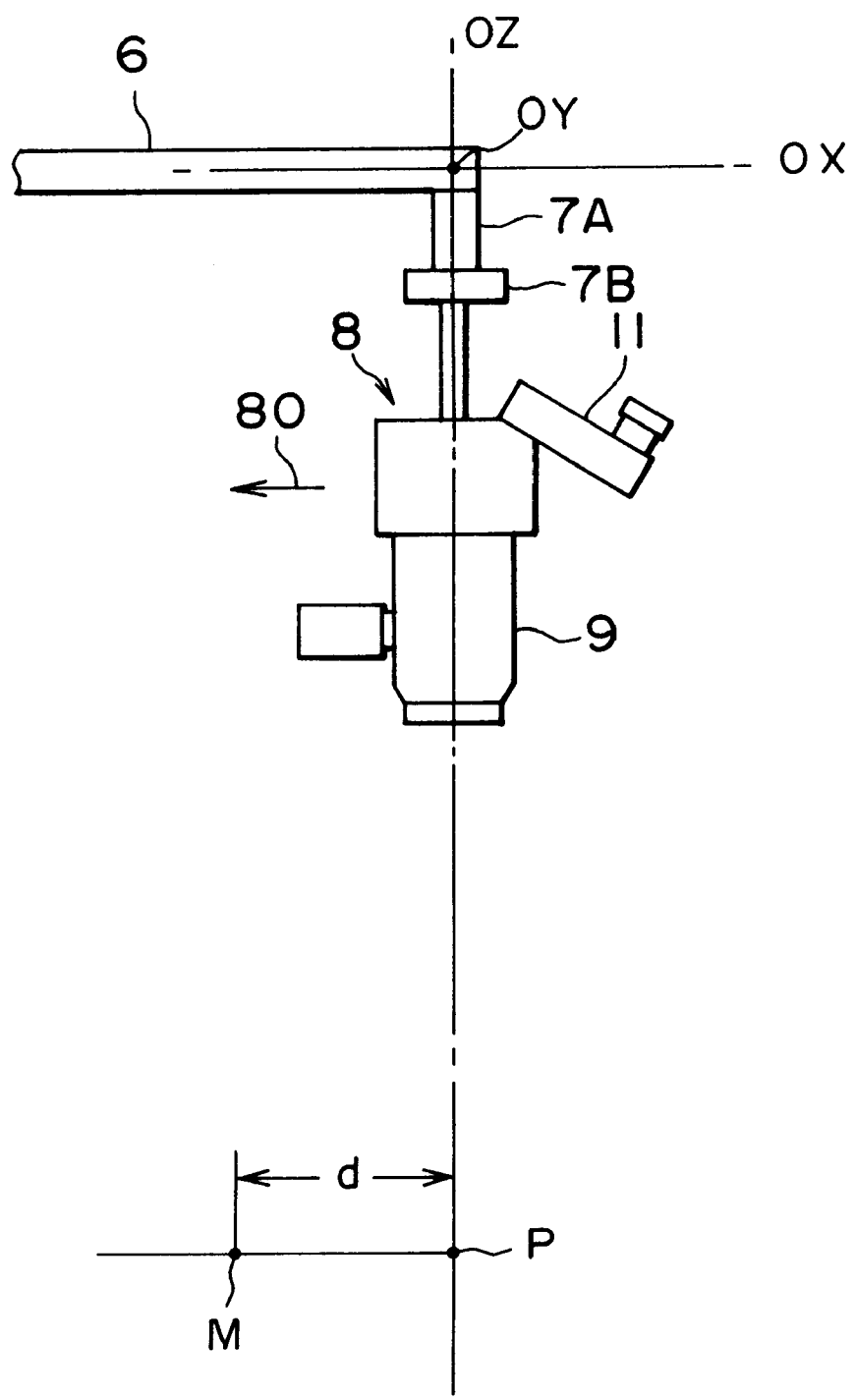
FIG. 6 is a diagram for explaining changing of observation magnification in the embodiment of the present invention.

In the case that the observation magnification of the main microscope body 8 is 1, as shown in FIG. 6, the main microscope body 8 is moved in a parallel manner along the rotation axis OX in a direction of an arrow 80 during a time period t by the horizontal direction moving unit 7B. As a result, the observation field is moved, so that the focal point of the main microscope body 8 is moved from a point P to a point M. When the focal point is moved from the point P to the point M while the observation magnification is 1, assuming that a distance between the point P and the point M is d, an apparent velocity v1 of the observation field (focal point) is expressed by v1=d/t.

In the case wherein the lens 20a of the variable power optical system 20 is relatively slid along the optical axis direction with respect to the lens 20b by the motor 44 and the observation magnification is changed from 1 to 2, as described above, when the main microscope body 8 is moved in a parallel manner along the rotation axis OX in a direction of the arrow 80 during a time period t, the distance moved by the main microscope body 8 is not different from that in the case that the observation magnification is 1. However, an apparent distance between the point P and the point M (namely, distance in observation field) is changed into 2d. Therefore, when the observation magnification is 2, the apparent velocity v2 of the observation field is expressed by v2=2d/t, thus, the apparent velocity of the observation field of the main microscope body 8 is faster than that in the case that the observation magnification is 1.

As a consequence, the variable power quantity corresponding to the observation magnification of 2 caused by the motor 44 is detected by the variable power encoder 57, and then the detection result of the variable power encoder 57 is output via the CPU 61 to the arithmetic-logic unit 63. The drive condition with respect to the main microscope body 8 is calculated by the arithmetic-logic unit 63 in such a manner that the apparent velocity v2 of the observation field when the observation magnification is 2 is equal to the apparent velocity v1 when the observation magnification is 1.

The CPU 61 controls the horizontal direction moving unit 7B based on the drive condition calculated by the arithmetic-logic unit 63, so as to move the main microscope body 8 in such a way that the apparent velocity v2 of the observation field when the observation magnification is 2 is equal to the apparent velocity v1 when the observation magnification is 1, namely, ½ of the apparent velocity v2. As a result, the constant apparent velocity of the observation field can be automatically maintained even if the observation magnification of the observation field is changed.

As described above, when the apparent velocity of the observation field is kept constant, an operator may freely determine how to set the apparent velocity of the main microscope body 8 on the basis of any magnification, and can arbitrarily set it.

Figure 7:
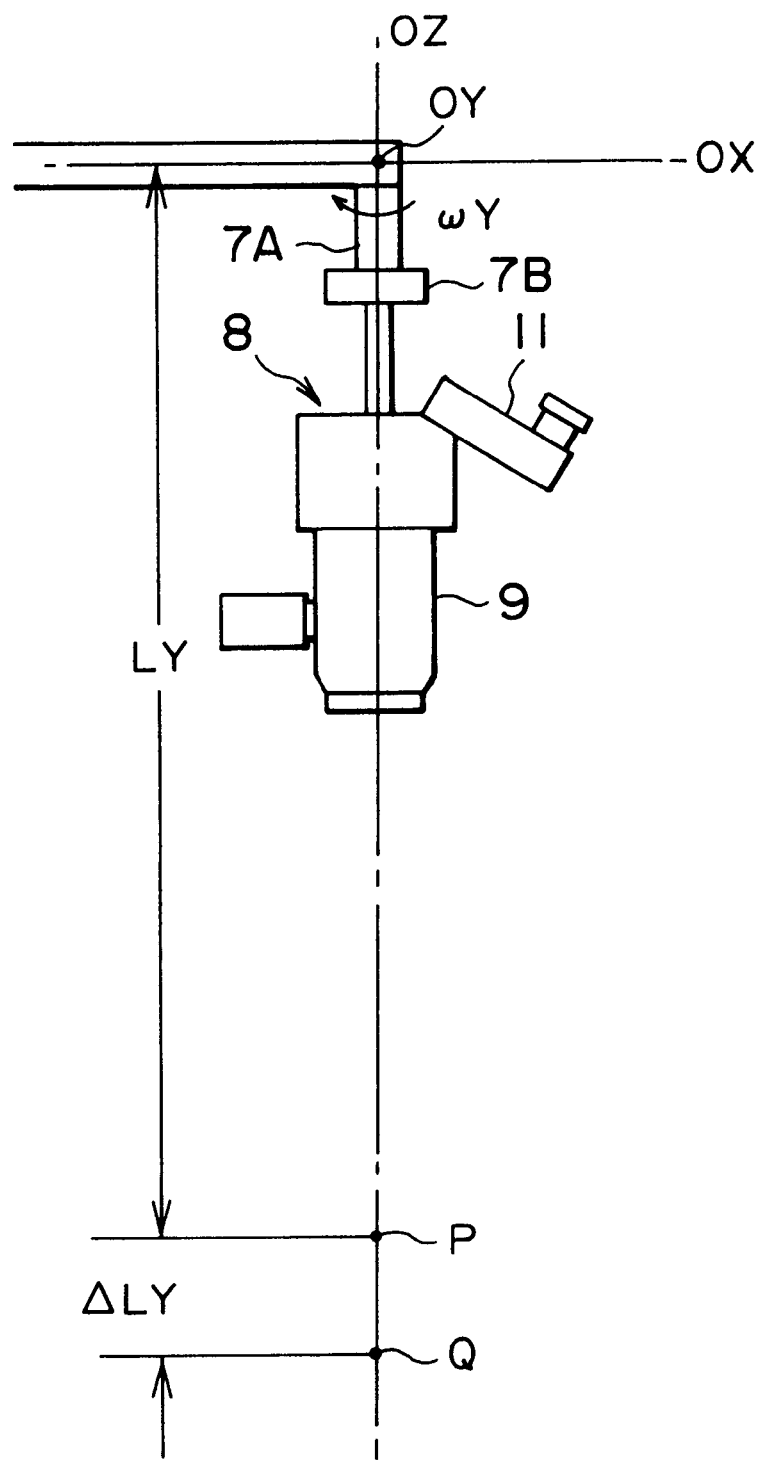
FIG. 7 is a diagram for explaining changing operation of a focal point in the embodiment of the present invention.

Referring to FIG. 7, a description will be made of operations in the case that a focal point is changed along the vertical direction.

As shown in FIG. 7, in the case wherein the point P is just focused by the main microscope body 8, assuming that a distance between the point P and the rotation axis OY is LY and an angular velocity about the rotation axis OY is ωY, the apparent velocity v3 of the observation field and the main microscope body 8 is expressed by v3=ωY×LY, with the rotation axis OY by the Y-axis actuator 51 as the rotation center, for example.

Next, in order to observe such a point Q that a distance from the rotation axis OY is LY+ΔLY, the vertical direction moving unit 7A is driven to cause the main microscope body 8 to lower, so that the focal point of the main microscope body 8 is made coincident with the point Q. At this time, as described above, similar to the above case that the focal point is the point P, when the main microscope body 8 and the observation field are moved at the angular velocity ωY by the Y-axis actuator 51, the apparent velocity v4 thereof is expressed by v4=ωY (LY+ΔLY). Therefore, in the case that the focal point is the point Q, the apparent velocity of the observation field is faster than that in the case that the focal point is the point P.

As a consequence, when the focal point is moved from the point P to the point Q, the amount of movement by the vertical direction moving unit 7A is detected by the vertical direction encoder 55. The detection result is output via the CPU 61 to the arithmetic-logic unit 63. The arithmetic-logic unit 63 calculates an angular velocity ωY' functioning as a drive condition that the apparent velocity v4 is equal to the apparent velocity v3 based upon the detection result from the vertical direction encoder 55. In this case, the angular velocity ωY' is obtained by the calculation which can satisfy the equation ωY×LY=ωY'×(LY+ΔLY).

Then, the CPU 61 controls the Y-axis actuator 51 based on the angular velocity ωY' functioning as the drive condition calculated by the arithmetic-logic unit 63 to keep both the apparent velocity of the main microscope body 8 and the apparent velocity of the observation field constant. As a result, even if the focal position of the observation field is changed, the apparent velocity of the observation field can be automatically kept constant.

As to the above changing operation of the focal point, a similar effect may be achieved in changing operation of the focal distance by the objective lens 10 in addition to the above case. In this alternative case, the angular velocity ωY' functioning as the drive condition which can satisfy the apparent velocity requirement v3=ωY'×(LY+ΔLY) may be calculated by the arithmetic-logic unit 63 based on a detection result obtained by the objective lens encoder 58 when the focal distance is changed.

As described above, when the apparent velocity of the observation field is kept constant, the operator may freely determine how to set an angular velocity of the main microscope body 8 on the basis of the angular velocity at any focal positions, and can arbitrarily set it.

Next, with reference to FIG. 8, a description will be made of operations when the focal point is swung.

Figure 8:
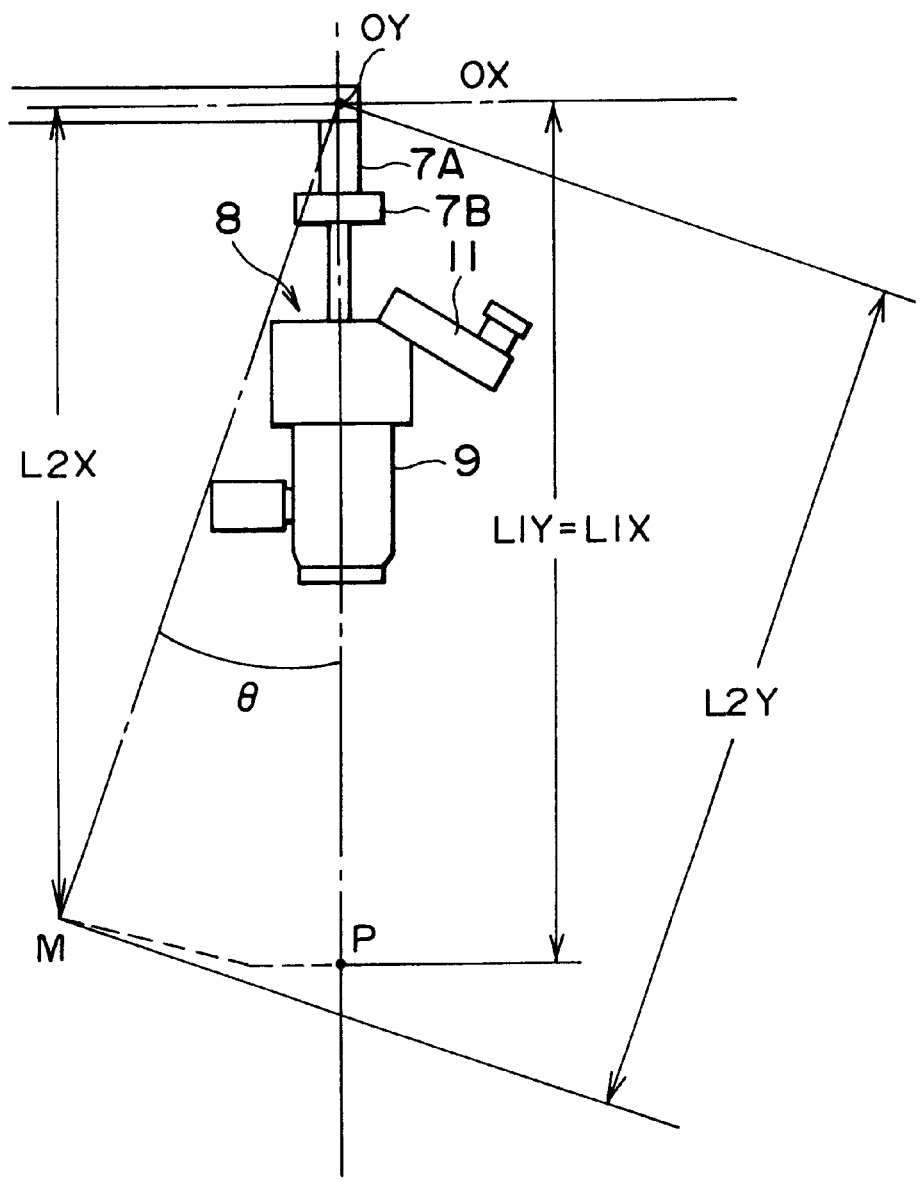
FIG. 8 is a diagram for explaining the case wherein an observation field is rotatively moved in the embodiment of the present invention.

As shown in FIG. 8, when the point P is just focused, assuming that a distance between the point P and the rotation axis OY is L1Y and a distance between the point P and the rotation axis OX is L1X, L1Y=L1X. Under this condition, the main microscope body 8 is moved by the Y-axis actuator 51, thereby moving the focal point to the point M by an angle θ. Since this is a swing movement with respect to the rotation axis OY, a distance L2Y between the point M and the rotation axis OY is expressed as L2Y=L1Y. On the other hand, a distance L2X between the point M and the rotation axis OX is expressed as L2X=L2Y cos θ. In other words, the distance L2Y between the point M and the rotation axis OY is different from the distance L2X between the point M and the rotation axis OX.

Thus, when the main microscope body 8 is swung by the X-axis actuator 52 around the rotation axis OX in the state that the point M is just focused, since a distance between the rotation axis OX and the focal point is changed in comparison with the case that the point P is focused, there is a shift in the apparent velocity of the observation field.

Also, when, after the main microscope body 8 is swung by the X-axis actuator 52 around the rotation axis OX as a rotation center, the main microscope body 8 is swung by the Y-axis actuator 51 around the rotation axis OY as a rotation center, there is a shift in the apparent velocity of the observation field.

As described above, when the observation is performed by a combination of the movement of the main microscope body 8 by the Y-axis actuator 51 and the movement of the main microscope body 8 by the X-axis actuator 52, there is a shift in the apparent velocity of the observation field. Therefore, an inclination angle with respect to the swing movement around the rotation axis OY and another incline angle with respect to the swing movement around the rotation axis OX are detected by the Y-axis encoder 53 and the X-axis encoder 54, respectively. Then, a drive condition is calculated by the arithmetic-logic unit 63 in such a manner that the apparent velocities of the observation fields in the swing movements around the rotation axis OY and OX are maintained as constant values.

Then, the CPU 61 controls the Y-axis actuator 51 and the X-axis actuator 52 based on this drive condition. As a result, it is possible to automatically keep the apparent velocities of the observation fields constant as to any directions of the rotation axis OY and OX.

Figure 9:
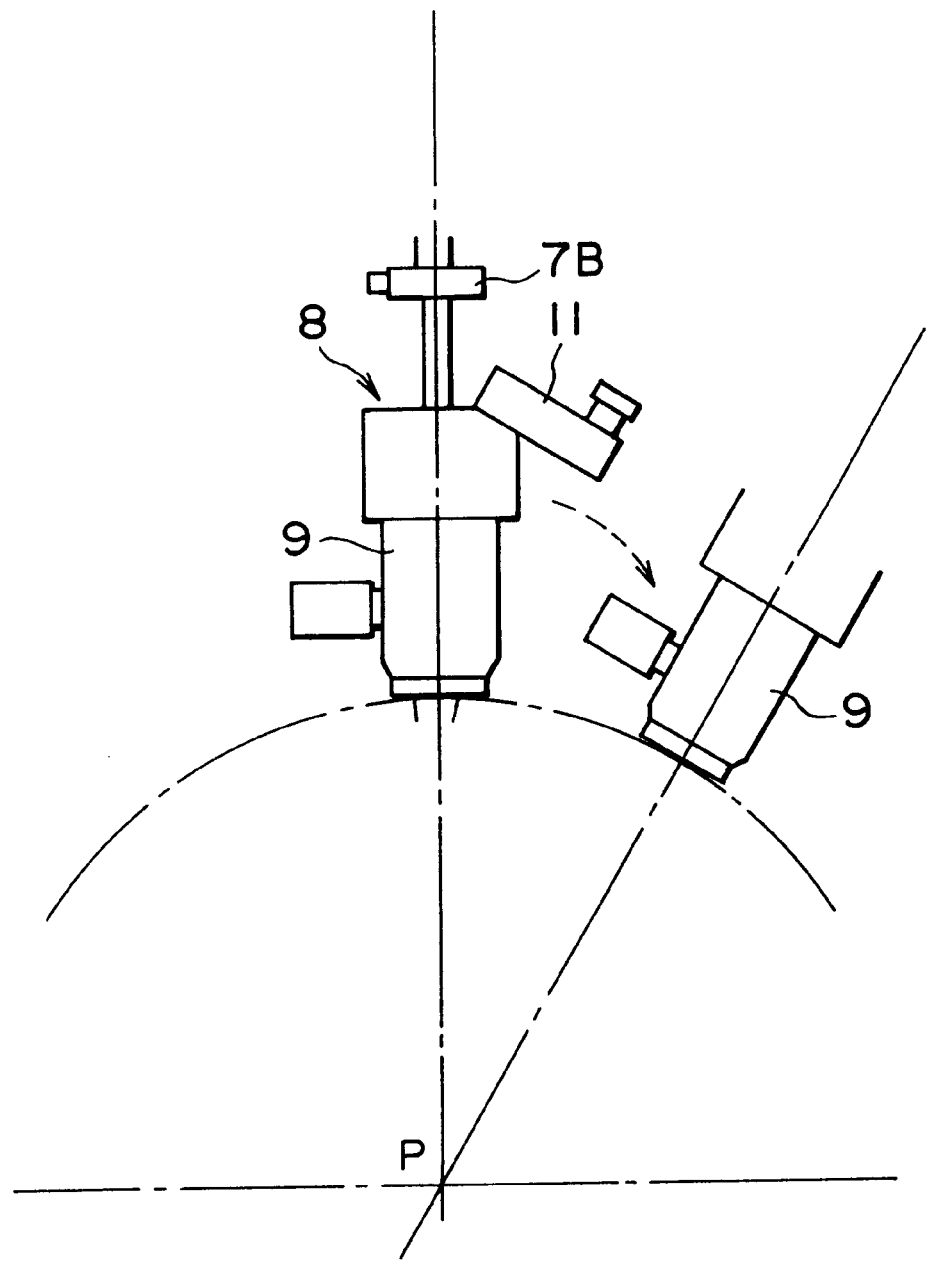
FIG. 9 is a diagram for explaining moving of an observation direction in the embodiment of the present invention.

Although the above operation has described such that the apparent velocity of the observation field can be kept constant, the operation microscope 1 according to this embodiment may also keep, as shown in FIG. 9, the apparent velocity of changes in the observation direction constant without moving the focal position.

In this case, a basic operation is similar to the above operation. That is, in such a case that the observation condition such as the observation magnification is changed, the respective drive conditions for the Y-axis actuator 51, the X-axis actuator 52, the vertical direction moving unit 7A and the horizontal direction moving unit 7B are calculated by the arithmetic-logic unit 63 in order that the apparent velocity of the observation direction before and after the observation condition is changed is constant. Based upon the calculated drive conditions, the CPU 61 controls the Y-axis actuator 51, the X-axis actuator 52, the vertical direction moving unit 7A and the horizontal direction moving unit 7B. Accordingly, it is possible to automatically keep the apparent velocity of changes in the observation direction constant in a similar manner to the above observation field.

Referring to flow charts shown in FIGS. 10 and 11, the variable power operation and the variable power detecting operation performed by the variable power optical system 20 and the variable power encoder 57 will be described in more detail as an example when a suitable velocity of the horizontal direction moving unit 7B is obtained based on a variable power quantity of the variable power optical system 20.

Figure 10:
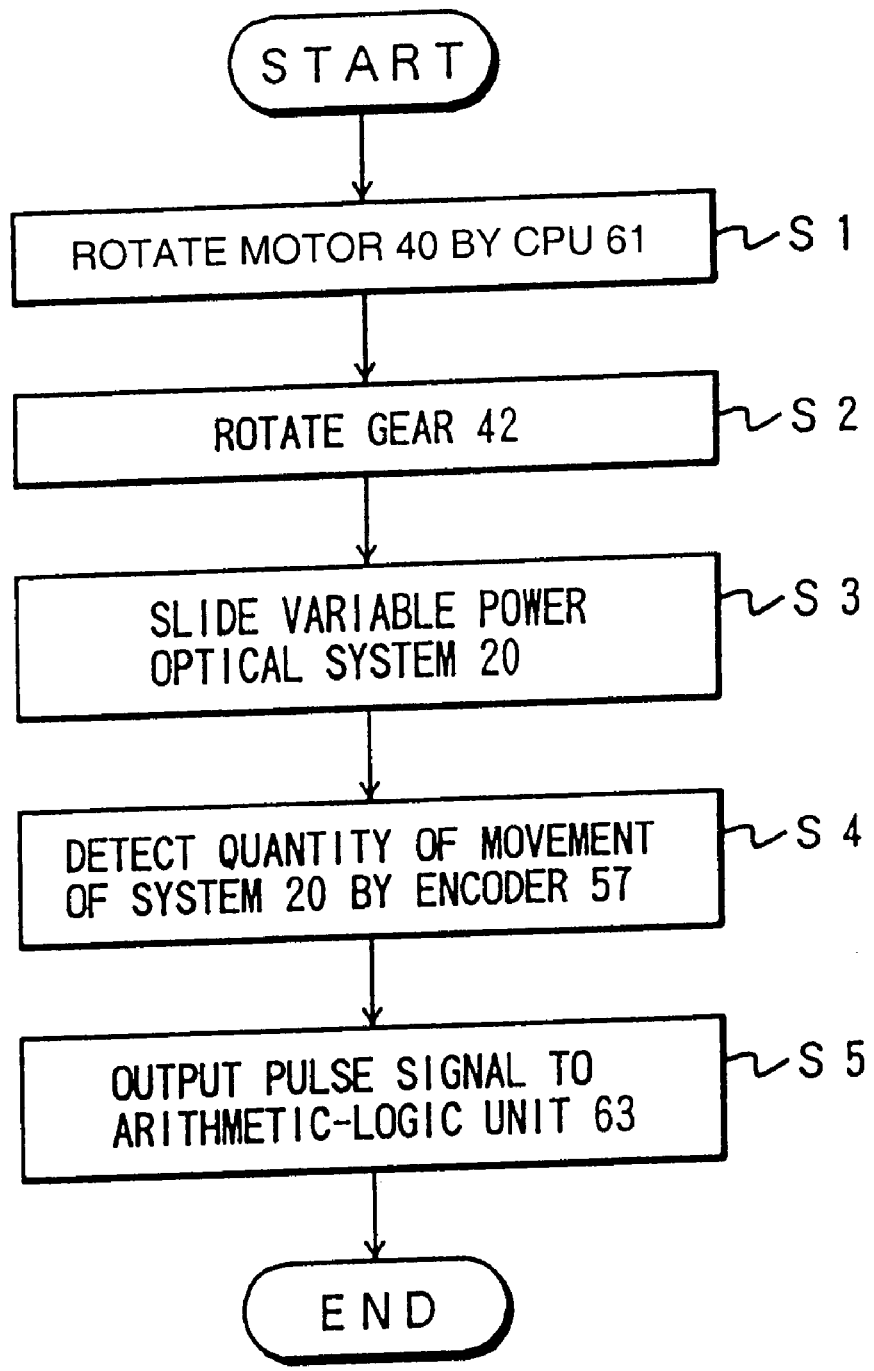
FIG. 10 is a flow chart for changing operation of observation magnification in the embodiment of the present invention.

FIG. 10 is a flow chart describing the variable power operation and the variable power detecting operation by the variable power optical system 20 and the variable power encoder 57. When a variable power instruction command is input from the foot switch 50 by an operator or the like, the motor 44 is rotation-operated under control of the CPU 61 (step S1). In response to this rotation operation of the motor 44, the gear 45 is rotated and then the gear 42 meshed with the gear 45 is also rotation-operated (step S2). Thus, the cylinder portion 40 is relatively slid along the optical axis direction with respect to the cylinder portion 41, and further the lens 20a arranged within the cylinder portion 40 is also relatively slid along the optical axis direction with respect to the lens 20b (step S3). When the lens 20a is moved, the variable power encoder 57 detects the moving quantity of the lens 20a (step S4), and then the moving quantity is converted into a pulse signal, so that the pulse signal is output via the CPU 61 to the arithmetic-logic unit 63 (step S5).

By the above operation, the arithmetic-logic unit 63 can calculate the drive condition in connection with the variable power operation by the variable power optical system 20.

Figure 11:
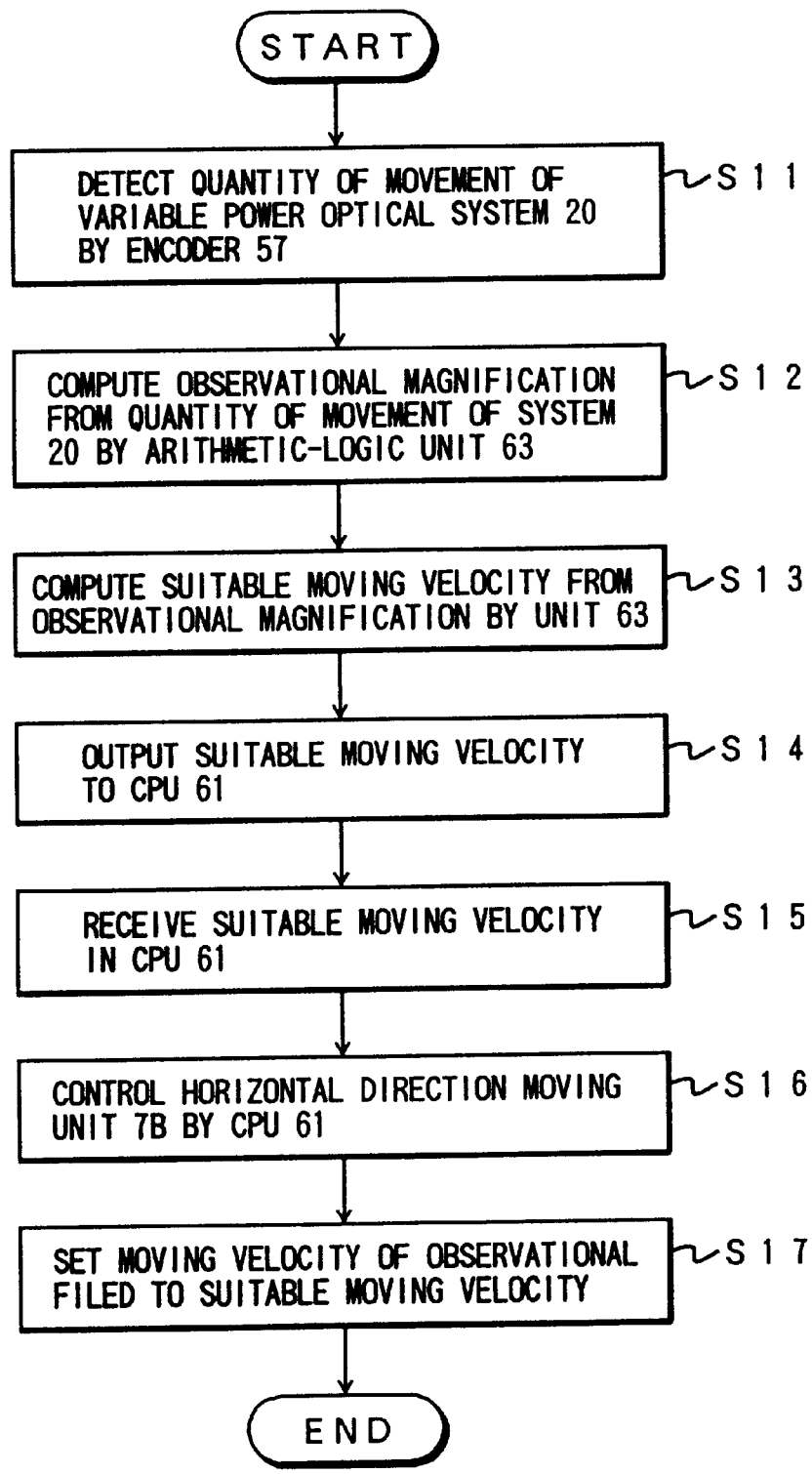
FIG. 11 is a flow chart for variable power operation and horizontal direction moving operation in the embodiment of the present invention.

FIG. 11 is a flow chart for describing an operation when the suitable velocity of the horizontal direction moving unit 7B is obtained based upon the variable power quantity of the variable power optical system 20. When an operator microscopically observes an eye E to be examined by using the operation microscope 1 under an observation magnification u1 and a velocity v1, the observation magnification u1 and the velocity v1 are stored in the memory unit 64 under control of the CPU 61.

When the operator changes the observation magnification u1 into the observation magnification u2, the lens 20a of the variable power optical system 20 is moved under control of the CPU 61, to thereby change the observation magnification. The variable power encoder 57 detects the amount of movement of the variable power optical system 20 (step S11), and outputs the detected amount of movement to the arithmetic-logic unit 63 via the CPU 61.

The arithmetic-logic unit 63 obtains the changed observation magnification based upon the detected amount of movement (step S12), calculates a suitable horizontal direction velocity (drive condition) v2 with respect to the obtained observation magnification u2 (step S13) and then outputs the calculated suitable horizontal direction velocity v2 to the CPU 61 (step S14). In the arithmetic-logic unit 63, the suitable horizontal direction velocity v2 is calculated based on an inverse proportional equation such as v2=v1× u1/u2. Then, the calculated suitable horizontal direction velocity v2 and observation magnification u2 are stored in the memory unit 64 so as to be prepared for the next movement of the observation field.

The CPU 61 receives the suitable horizontal direction velocity v2 calculated by the arithmetic-logic unit 63 (step S15) and controls the horizontal direction moving unit 7B in such a manner that the main microscope body 8 is moved at the suitable horizontal direction velocity v2 (step S16). As a result, the velocity of the observation field is set as the suitable horizontal direction velocity v2 (step S17).

As described above, the arithmetic-logic unit 63 calculates the suitable horizontal direction velocity in accordance with the observation magnification changed by the variable power optical system 20. Then the horizontal direction moving unit 7B is operated under control of the CPU 61 based on this calculation result so as to move the main microscope body 8. Thus, even if the observation magnification is changed, the operability of the operation microscope can be improved while maintaining the suitable velocity of the observation field without requiring cumbersome adjustments.

The present invention is not limited to the above embodiments, but may be modified, changed, and substituted without departing from the technical spirit and scope of the present invention.

The equation related to the calculation of the suitable horizontal direction velocity (drive condition) may be expressed as a linear equation made from a velocity v and an observation magnification u by an inverse proportional equation such as v=a/u+b, where a and b are constants. Alternatively, a proportional equation simply made from v=−a×u+b (a and b are constants) may be employed as an alternative to the inverse proportional equation. The related equations are not limited to such linear equations as the proportional equation and the inverse proportional equation, but may be expressed by using other equations.

When the amount of movement of the variable power optical system 20 is detected and then the detected amount of movement is output to the arithmetic-logic unit 63, the pulse signal supplied to the motor 44 may be directly output to the arithmetic-logic unit 63.

Figure 12:
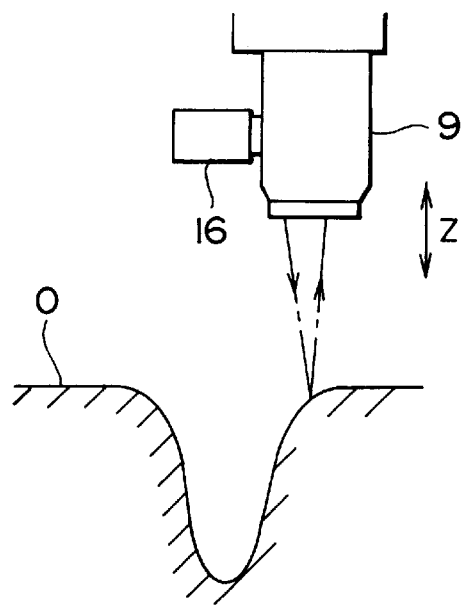
FIG. 12 is a diagram for explaining the case wherein the observation field is shallow in the embodiment of the present invention.
Figure 13:
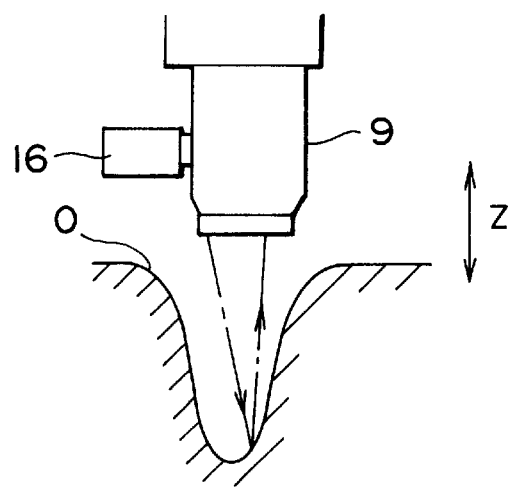
FIG. 13 is a diagram for explaining the case wherein the observation field is deep.
Figure 14:
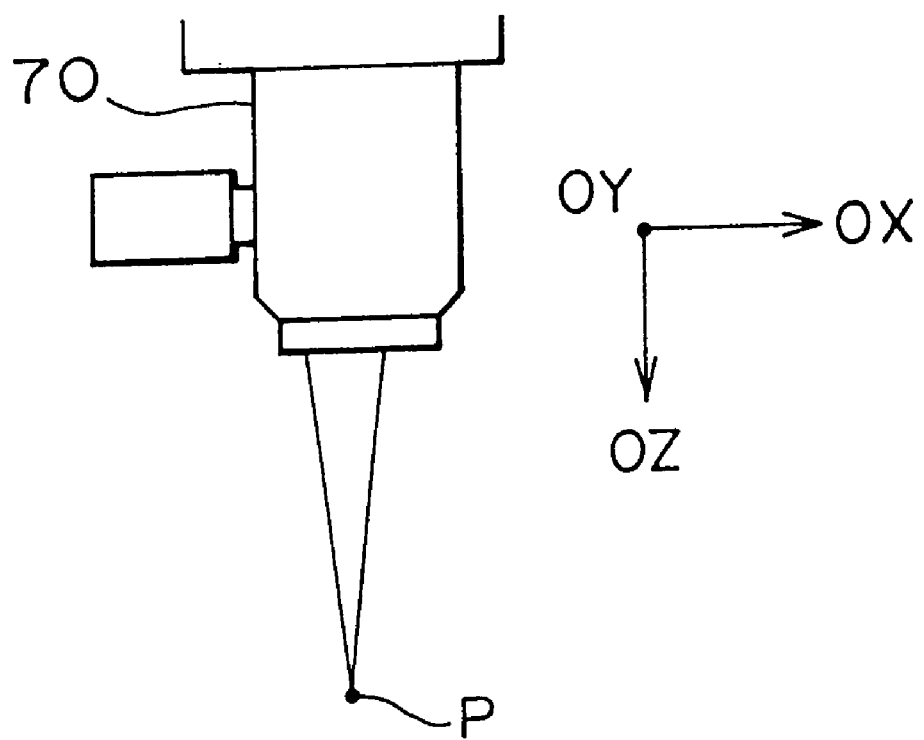
FIG. 14 is a diagram for explaining moving of a main microscope body of a commonly used operation microscope.

For example, as shown in FIG. 12, in the case that the observation magnification is decreased by the operator or the like in order to observe a wide observation field (the affected part O in FIGS. 12 and 13) in a shallow depth, a rapid velocity for the main microscope body 8 is set. To the contrary, as shown in FIG. 13, in the case that the observation magnification is increased by the operator or the like so as to observe a narrow observation field in a deep depth, a slower velocity for the main microscope body 8 is set. By such setting, it is possible to maintain the velocity of the observation field without having a sense of incongruity for the operator, so that the medical operation can be quickly carried out.

Also, the above mechanism for maintaining the constant apparent velocity of the observation field and the constant apparent velocity of the observation direction, according to the present invention, may be applied to, for example, the stand apparatus as described in Japanese Patent Examined Publication No. 2-56890. That is, when the above actuators are provided on the stand apparatus in order to change the observation direction or the like, the present invention is very convenient. In this stand apparatus, the balance is kept by using the counter weight, and the rotation shaft is arranged in such a manner that the main microscope body is moved around the focal point as the rotation center. As a result, the medical operation time may be shortened when this mechanism is applied to the stand apparatus.

As described above, according to the present invention, the drive condition is selected such that a predetermined apparent velocity of movement of the observation field is obtained, and then the movement of the main microscope body is controlled based on this drive condition. Therefore, it is possible to provide the operation microscope capable of automatically maintaining the constant apparent velocity of the observation field, improving the operability and shortening the medical operation time even if the observation condition such as the focal position and the observation magnification or the observation state are changed.

Also, according to the present invention, the drive condition is selected such that a predetermined apparent velocity of change in the observation direction is obtained, and then the movement of the main microscope body is controlled based on this drive condition. Therefore, it is possible to provide the operation microscope capable of automatically maintaining the constant apparent velocity of change in the observation direction, improving the operability and shortening the medical operation time even if the observation condition such as the focal position and the observation magnification or the observation state are changed.

What is claimed is:

1. An operation microscope having a moveable observation field comprising:

a main microscope body supported by a support member and being moveable relative to the support member by rotation about a plurality of rotation axes;

means for rotating the main microscope body about one or more of the rotation axes to move the main microscope body from a first observation field position to a second observation field position different from the first observation field position;

means for setting a value for an apparent velocity of movement of the observation field to a desired value;

means for monitoring a position of the main microscope body;

means for calculating a drive condition that maintains the apparent velocity of the moveable field at the value set using the means for setting a value for the apparent velocity when the main microscope body is moved from the first observation field position to the second observation field position; and means for controlling the rotating means in accordance with the calculated drive condition.

2. The operation microscope according to claim 1, wherein the main microscope body comprises a variable power optical system for producing a variable observation magnification, further comprising means for monitoring the observation magnification, wherein the means for calculating calculates a drive condition that maintains the apparent velocity of movement of the observation field at the value set using the means for setting a value for the apparent velocity when the observation magnification is changed.

3. The operation microscope according to claim 1, wherein the main microscope body comprises an object lens optical system having a changeable focal distance, further comprising means for monitoring the focal distance of the object lens optical system, wherein the means for calculating calculates a drive condition that maintains the apparent velocity of movement of the observation field at the value set using the means for setting a value for the apparent velocity when the focal distance of the object lens optical system is changed.

4. The operation microscope according to claim 1, further comprising means for varying a focal position of the main microscope body with respect to the plurality of rotation axes and means for monitoring the focal position of the microscope body, wherein the means for calculating calculates a drive condition that maintains the apparent velocity of movement of the observation field at the value set using the means for setting a value for the apparent velocity when the focal position of the main microscope body is changed.

5. The operation microscope according to claim 1, further comprising means for monitoring a focal position of the microscope body relative to the plurality of rotation axes, wherein the means for calculating calculates a drive condition that maintains the apparent velocity of movement of the observation field at the value set using the means for setting a value for the apparent velocity when the focal position of the main microscope body is changed.

6. An operation microscope having a changeable observation direction comprising:

a main microscope body supported by a support member and being moveable relative to the support member by rotation about a plurality of rotation axes;

means for rotating the main microscope body about one or more of the rotation axes to move the main microscope body from a first observation direction to a second observation direction different from the first observation direction;

means for setting a value for an apparent velocity of change in the observation direction to a desired value;

means for monitoring a position of the main microscope body;

means for calculating a drive condition that maintains the apparent velocity of the change in observation direction at the value set using the means for setting a value for the apparent velocity when the main microscope body is moved from the first observation direction to the second observation direction; and means for controlling the rotating means in accordance with the calculated drive condition.

7. The operation microscope according to claim 6, wherein the main microscope body comprises a variable power optical system for producing a variable observation magnification, further comprising means for monitoring the observation magnification, wherein the means for calculating calculates a drive condition that maintains the apparent velocity of the change in observation direction at the value set using the means for setting a value for the apparent velocity when the observation magnification is changed.

8. The operation microscope according to claim 6, wherein the main microscope body comprises an object lens optical system having a changeable focal distance, further comprising means for monitoring the focal distance of the object lens optical system, wherein the means for calculating calculates a drive condition that maintains the apparent velocity of the change in the observation direction at the value set using the means for setting a value for the apparent velocity when the focal distance of the object lens optical system is changed.

9. The operation microscope according to claim 6, further comprising means for varying a focal position of the main microscope body with respect to the plurality of rotation axes and means for monitoring the focal position of the microscope body, wherein the means for calculating calculates a drive condition that maintains the apparent velocity of the change in the observation direction at the value set using the means for setting a value for the apparent velocity when the focal position of the main microscope body is changed.

10. The operation microscope according to claim 6, further comprising means for monitoring a focal position of the microscope body relative to the plurality of rotation axes, wherein the means for calculating calculates a drive condition that maintains the apparent velocity of the change in the observation direction at the value set using the means for setting a value for the apparent velocity when the focal position of the main microscope body is changed.

* * * * *